(12) United States Patent
Kodama et al.

(10) Patent No.: US 6,235,709 B1
(45) Date of Patent: May 22, 2001

(54) INHIBITOR OF *HELICOBACTER PYLORI* COLONIZATION

(75) Inventors: Yoshikatsu Kodama, Gifu; Nobutake Kimura, Saitama, both of (JP)

(73) Assignee: Ghen Corporation, Gifu (JP)

( * ) Notice: Subject to any disclaimer, the term of this patent is extended or adjusted under 35 U.S.C. 154(b) by 0 days.

(21) Appl. No.: 09/458,996

(22) Filed: Dec. 10, 1999

(30) Foreign Application Priority Data

Dec. 11, 1998 (JP) .................................................. 10-352767

(51) Int. Cl.$^7$ ..................................................... A61K 38/00
(52) U.S. Cl. ........................ 514/2; 514/7; 514/8; 514/55; 514/56; 514/24; 536/2; 536/4.1; 536/123; 536/123.1
(58) Field of Search .................................. 514/2, 24, 7, 8, 514/55, 56; 536/2, 4.1, 123, 123.1

(56) References Cited

U.S. PATENT DOCUMENTS 5,679,375 * 10/1997 Spilburg et al. ...................... 424/451
5,753,630 * 5/1998 Zopf et al. ............................. 514/25
5,804,549 * 9/1998 Blackburn et al. ....................... 514/2

OTHER PUBLICATIONS

Simon et al, Infection and Immunity, vol. 65, No. 2, pp. 750–757, Feb. 1997.*
Nakao et al, Am. J. Gastreoenterol., vol. 92, No. 6, pp. 1005–1011 (abstract), Jun. 1997.*
Dial et al, Dig. Dis. Sci., vol. 43, No. 12, pp. 2750–2756 (abstract), Dec. 1998.*
Hirmo et al, FEMS Immunol. Med. Microbiol., vol. 20, No. 4, pp. 275–281 (abstract), Apr. 1998.*
Ota et al, Virchows Archiv, vol. 433, No. 5, pp. 419–426 (abstract), May 1998.*
Barresi et al, Virchows Arch, vol. 435, pp. 458–459, 1999.*
Icatlo et al, Gastroenterol., vol. 119(2), pp. 358–367, 2000.*
Icatlo et al, Microbiol. Immunol., vol. 44(9), 2000.*
Hirmo et al, FEMS Immunology and Medical Microbiology, vol. 20, pp. 275–281, 1998.*
Clyde et al, Infect. Immune., vol. 61, pp. 40511–40517, 1993.*

* cited by examiner

*Primary Examiner*—James H. Reamer
(74) *Attorney, Agent, or Firm*—Burns, Doane, Swecker & Mathis, LLP

(57) ABSTRACT

The present invention provides a safe and effective inhibitor of *Helicobacter pylori* colonization in the stomach and a food containing the inhibitor. The inhibitor of the present invention comprises as an active ingredient a mucin, especially a mucin from milk of a cow or a mucin from albumen of an egg and is useful for the prevention or treatment of diseases caused by infection of *Helicobacter pylori* such as peptic ulcers.

16 Claims, 2 Drawing Sheets

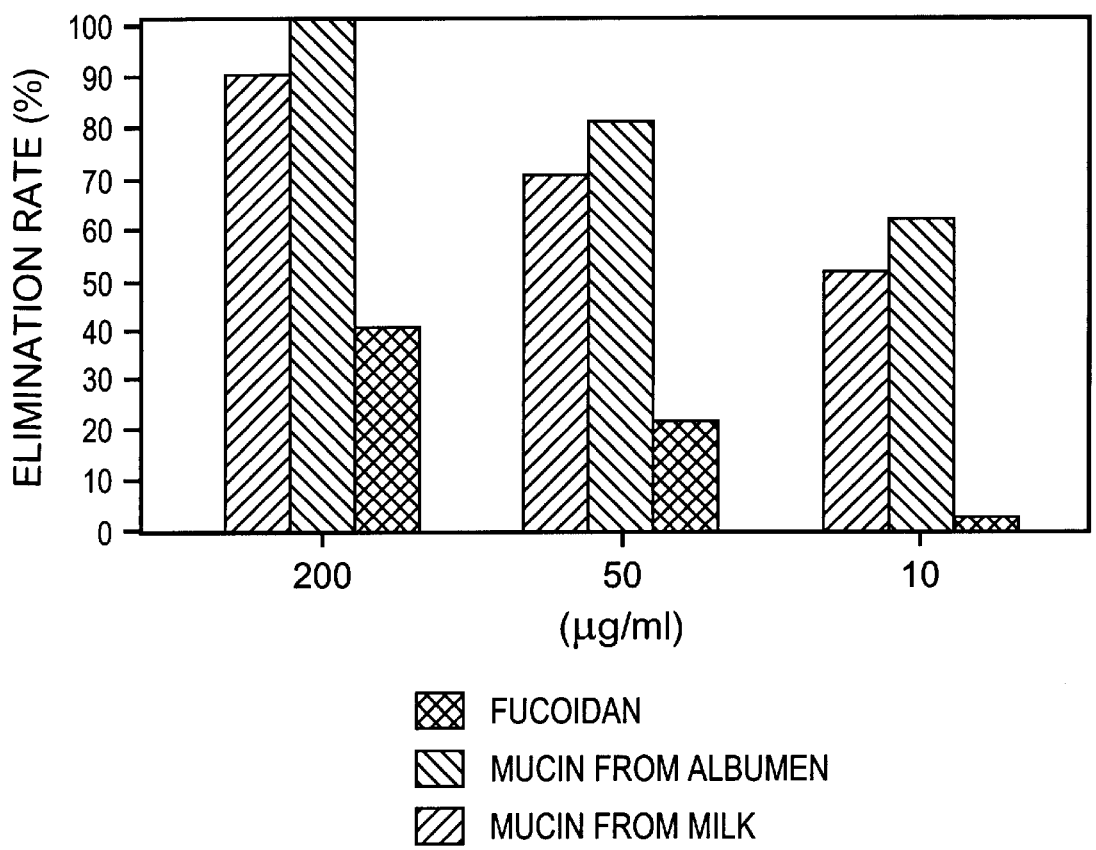

INHIBITOR OF *HELICOBACTER PYLORI* COLONIZATION

TECHNICAL FIELD

The present invention relates to an inhibitor of the colonization of *Helicobacter pylori* (hereinafter referred to as *H. pylori* or Hp) which is associated with the occurrence of peptic ulcers, which inhibitor is capable of eliminating *H. pylori* from the stomach, and a food containing the inhibitor, especially an anti *H. pylori* functional food.

BACKGROUND OF THE INVENTION

At present it is believed that eradication of *H. pylori* from the stomach is essential for treating peptic ulcers fully. The combination of an antibiotic and an inhibitor of gastric acid secretion has been generally proposed as a therapy for eradication of *H. pylori* as described below.

*H. pylori* is a gram-negative spiral rod-shaped bacterium having some flagella at one end and inhabiting the human gastric mucosa. Marshall, B. J. and Warren, J. R. in Australia reported in 1983 that this bacterium was frequently detected in stomach biopsy specimens from patients with gastric ulcers. At that time this bacterium was named *Campylobacter pylori* since it resembles Campylobacter in morphology and growth characteristics. Later, it was found that the bacterium is different from Campylobacter in the fatty acid composition of its outer membrane and sequence of ribosome 16S-RNA. Therefore, the bacterium is now referred to as *Helicobacter pylori* and belongs to the newly established genus of Helicobacter.

Since then, many reports have been published based on epidemiological studies, indicating that this bacterium causes gastritis, gastric ulcers, and duodenal ulcers and is associated with diseases such as gastric cancer. Once Hp colonizes gastric mucosa, it cannot be eradicated in the stomach and continues to inhabit the stomach, although the immune response to infection thereof is strong, i.e., the antibody titer is high. Therefore, unless Hp is completely eliminated from the stomach by antibiotic therapy, the infection will return to the same level as before treatment within about a month after the administration of antibiotics is stopped. Additionally, the pH of the stomach is maintained very low by HCl, which is a strong acid, and therefore most antibiotics are apt to be inactivated. For this reason, the combination of an antibiotic and a proton pump inhibitor which strongly suppresses the secretion of gastric acid is utilized often in a greater dose than usual for eradication of *H. pylori*. Recently, a new treatment employing a combination of bismuth subsalicylate, metronidazole, and tetracycline has proved to have the highest rate of elimination of Hp, but metronidazole in the combination is known to cause the rapid emergence of an antibiotic-resistant strain when used alone. In developing countries, this medicine has been used widely for treating diarrhea patients, and as a result there is a high rate of infection with metronidazole-resistant Hp.

Thus, the administration of antibiotics for a long time has the serious problems of increasing antibiotic-resistant strains as well as causing side effects.

At present, an immunological therapy approach using an oral vaccine has been proposed in order to solve problems such as side effects and increase of antibiotic-resistant strains by treatment with antibiotics for the eradication of the bacteria. For this purpose it is essential to develop model animals for Hp infection. However, Hp cannot easily infect small animals such as mice or rats, and germ-free animals are required for infection. Also, fresh isolates are required for maintaining infection for a long time. These requirements have obstructed studies aimed at developing new methods for prevention and treatment. Also, the oral vaccine preparation usually has heat-labile toxin (LT) derived from *E. coli* and cholera toxin, and mucosal immunity cannot be attained without these adjuvants. In respect to safety in practical application, LT from *E. coli* and cholera toxin have a high level of toxicity, and the oral vaccine method has unsolved problems in its practical application to humans. Furthermore, the vaccine is predominantly used for prevention, and therefore it has no effect on patients who have already been infected with Hp.

As a new attempt to inhibit Hp, the use of specific antibodies is proposed, which antibodies are obtained from the eggs of hens immunized against Hp whole cells as an antigen. However, complete elimination of Hp from the stomach using antibodies against whole cells of Hp cannot be expected. Also, the actual effect on elimination of Hp from the stomach has not been confirmed.

On the other hand, it is disclosed that cells of certain bifid bacteria or lactic acid bacteria, and polysaccharides extracted from these cells are useful in prevention or treatment of gastric ulcers (Japanese Patent Application Kokai No. 4-5236), and that polysaccharide of rhamnose, ramnan, derived from certain seaweed and oligosaccharide of rhamnose are useful as an antiulcer (Japanese Patent Application Kokai No. 6-247861).

Japanese Patent Application Kokai No. 7-138166 describes the use of fucoidan, which is a polysaccharide derived from Nemacystus. This publication states that fucoidan inhibits the colonization of Hp in gastric mucosa and has antiulcer activity. However, ulcers induced with acetic acid, which are basically different from Hp-induced ulcers with respect to pathological development, are used in order to show the effects of treatment of ulcers in that publication. Therefore, in that publication, there is no evidence for suppressing the formation of ulcers caused by Hp infection. Furthermore, that publication states that fucose (monosaccharide) is considered to be a colonization factor (adhesin), and an in vitro experiment based on that assumption was performed using biotinylated fucose as an adhesion marker to see an inhibitory effect of fucoidan on Hp colonization. However, fucose is not considered to be an adhesin at present, so that experiment does not show an inhibitory effect of fucoidan on Hp colonization.

As explained above, the long-term use of antibiotics for elimination of Hp results in an increase in antibiotic-resistant bacteria as well as side effects, and a vaccine has not been developed for practical use. Also, attempts to use egg antibodies against Hp whole cells cannot eradicate Hp, and therefore are not effective for prevention or treatment; of gastritis, gastric ulcers, and duodenal ulcers.

SUMMARY OF THE INVENTION

It is an object of the present invention to provide an effective and safe inhibitor of Hp colonization which is associated with the occurrence of peptic ulcers, which inhibitor is capable of inhibiting the colonization of Hp effectively without the disadvantages of side effects and increase of drug-resistant strains which are associated with the use of antibiotics, and to provide a food for treating or preventing peptic ulcers, including a physiologically functional food and a food for medical use.

Other objects and advantages as well as the nature of the present invention will be apparent from the following description.

Generally, the first step for completion of an infection of a bacterium is adhesion of the bacterium to a host cell and colonization of the bacterium by growing there. For the bacterium to adhere to the host cell, an adhesin has to bind to a receptor on the surface of the host cell. The specificity of the infective site of the bacterium is determined by this adhesin and the receptor. If the receptor molecule coexists when the bacterium adheres to the host cell, competitive inhibition occurs and an infection does not occur.

An adhesin of Hp and a receptor on human gastric mucosa are supposed to be target molecules for inhibition of Hp infection. The present inventors clarified by studies regarding the mechanism of adhesion of Hp that the adhesin of Hp, which had not been elucidated, is urease produced by Hp. Furthermore, the present inventors demonstrated that the oral administration of antibodies obtained from chicken eggs against urease of Hp can remarkably suppress the growth of Hp in the stomach (Japanese Patent Application Kokai No. 10-287585).

The present inventors have studied substances capable of inhibiting the adhesion of urease to gastric mucosa and have found that mucins such as mucin derived from the milk of a cow or mucin derived from the albumen of a chicken egg are able to eliminate Hp which colonizes the stomach by specifically binding urease which is an adhesin localized on the surface layer of Hp cell, and thereby completed the present invention.

In one aspect, the present invention provides an inhibitor of *Helicobacter pylori* colonization, comprising a mucin other than a mucin derived from mammalian alimentary canal as an active ingredient. This inhibitor is useful for prevention and treatment of diseases caused by or associated with *Helicobacter pylori* in mammals including humans such as peptic ulcers. The mucin used in the present invention is preferably a mucin derived from the milk of a cow or a mucin derived from the albumen of a chicken egg.

The present invention also provides an inhibitor composition of *Helicobacter pylori* colonization, comprising a mucin other than a mucin derived from a mammalian alimentary canal and an inhibitor of gastric acid secretion.

In another aspect, the present invention provides a food comprising the above-mentioned inhibitor of *Helicobacter pylori* colonization. The mucin used in the present invention is preferably a mucin derived from the milk of a cow or a mucin derived from the albumen of a chicken egg. The mucin is preferably contained in an amount of 0.5–60% by weight of the food.

BRIEF DESCRIPTION OF THE DRAWINGS

FIG. 3 is a graph showing elimination rate of Hp in mice.

DETAILED DESCRIPTION OF THE PREFERRED EMBODIMENTS

Figure 1:
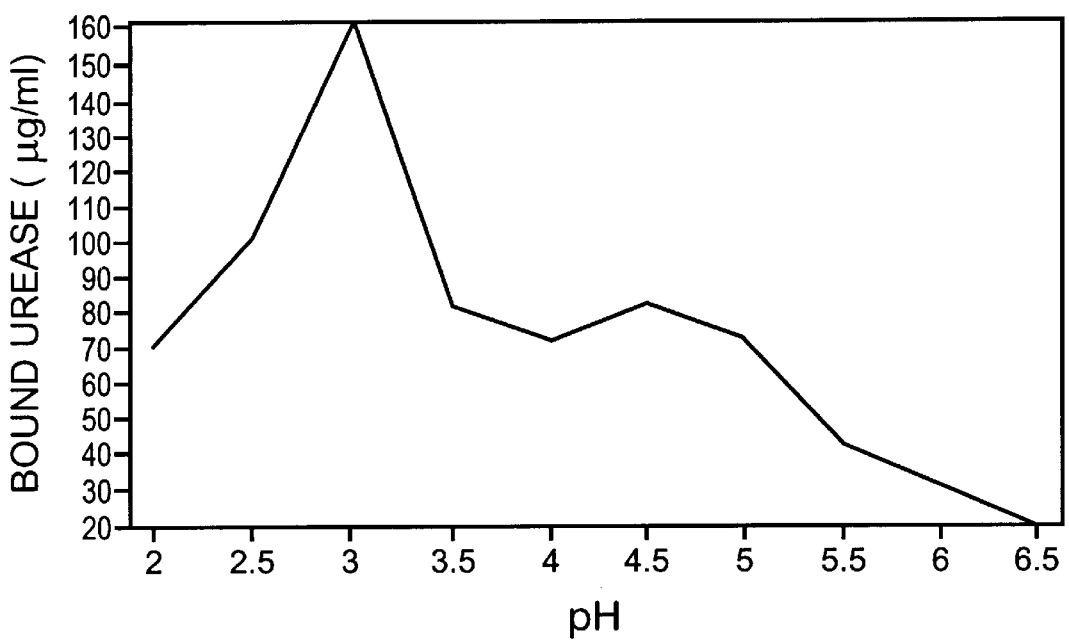
FIG. 1 is a graph showing adhesion pattern of urease to purified gastric mucin.

According to the present invention, a mucin other than a mucin derived from mammalian alimentary canal is used as an active ingredient in an inhibitor of *Helicobacter pylori* colonization.

Generally, a mucin is a mucous substance produced by mucous membrane or salivary gland of an animal, and comprises various glycoproteins. A mucin is also contained in colostrum and milk of a mammal and is contained in the albumen, chalaza and vitelline membrane of chicken eggs in large amounts.

Mucin is a giant polymer having an ultra-high molecular weight of $10^6$–$10^7$, and comprises 10–20% by weight of proteins and 80–90% by weight of carbohydrates. Mucin-type glycoprotein, which is a constitutive ingredient of mucin, is a conjugated protein in which sugar chains comprising D-galactose, sialic acid, L-fucose, N-acetyl-D-galactosamine, etc. are bound to peptides and which is characterized in that the sugar chains are bound to peptides by the binding of N-acetyl-D-galactosamine to hydroxyl groups of serine or threonine through O-glycosidic linkage. Part of the sugar chain contains a sulfate group.

The mucin used in the present invention may be any mucin other than a mucin derived from a mammalian alimentary canal, and includes mucins prepared from mammalian milk, and albumen, chalaza and vitelline membrane of poultry eggs. Preferably, mucins derived from the milk of a cow (hereinafter referred to as milk) or the albumen of chicken eggs are used in view of their effect.

When milk or albumen of chicken eggs is used as a starting material of mucin which is an active ingredient of the present inhibitor, these materials can be obtained inexpensively and in large quantities, and the isolation and purification of mucin therefrom can be carried out easily and by a simple procedure. In addition, mucin which has less contaminants such as enzymes and is of high purity can be prepared from the above material. Also, in preparing mucin from milk, whey can be used. Whey has been discarded without an effective way of utilization, although it is produced in large amounts as side-product during a process for preparing cheese and the like. Therefore, mucin can be prepared in large amounts industrially, and the use of mucin from milk is very advantageous in respect to cost and practical use.

Additionally, mucin in milk or albumen of chicken eggs is of high stability and does not lose its physiological activity due to heat or at a low pH, and therefore it can be readily recovered and purified from a starting material and is advantageous with respect to formulation into a food or medication, processing, and storing.

Milk contains substances having various physiological activities. For example, it has been reported that lactoferrin has various physiological activities such as antibacterial, antiviral and antitumor activities. As to mucin, which is a macro molecule comprising glycoprotein, only anti-rotavirus activity has been reported, and other physiological functions have not been reported.

It has been known for a long time that the proteins of chicken eggs (lysozyme, ovoinhibitor, avidin, ovotransferrin, etc.) have various physiological functions. Recently, it was reported that the protein obtained by digesting a protein of a chicken egg with protease exhibits anti-hypertensive activity, phagocytosis activity, etc. It has been also reported that ovomucin (a mucin derived from the albumen of a chicken egg) exhibits anti-rotavirus activity, and sulfated glycopeptide which exists in ovomucin, chalaza, and vitelline membrane activates macrophages to promote the release of tumor necrosis factors and cytokines and to kill only mammary tumors.

Any known method can be used for extraction, isolation and purification of mucin. Usually, mucin which exists in the mucous membrane or gel layer of the alimentary canal may be recovered by solubilizing mucin by homogenization or ultrasonic wave treatment and then isolating a fraction of high molecular weight by gel filtration or ethanol precipitation. Solubilization of mucin may be performed by extraction with guanidine hydrochloride, urea, a salt solution, or a surfactant or treatment with a reducing reagent or protease. Some kinds of mucin may be recovered by forming an insoluble complex with a quaternary ammonium salt or by precipitation under acidic conditions.

In the preparation of mucin from milk, for example, milk fat and casein may be removed from milk by a conventional method to obtain whey, lipoproteins may be then removed from the whey, and if necessary, concentration and dialysis may be carried out. The thus obtained substance containing mucin may be subjected to gel filtration using a Sepharose column, etc., treatment with a membrane, and the like to obtain purified mucin. If mucin having a low molecular weight is required, further treatment such as protease treatment, alkali hydrolysis, etc. may be conducted. Either colostrum or milk produced following colostrum can be used as milk.

Mucin may be prepared from the albumen of chicken eggs as follows. For example, concentrated albumen is separated from collected albumen, and a gelatinous portion is obtained by ultracentrifugation. Insoluble ovomucin prepared from this portion is solubilized by a procedure such as ultrasonic wave treatment or homogenization, and mucin is recovered from this by gel filtration, membrane treatment, or any other procedure. If necessary, purification may be further conducted by gel filtration, etc.

The mucin used in the present invention can inhibit the adhesion of urease produced by Hp to mucin of gastric mucosa as demonstrated in the following examples. Since urease is localized on the surface of Hp cells, the mucin of the present invention masks the adhesin, urease, by predominantly binding urease in the stomach and thereby inhibits the adhesion of Hp to the receptor of gastric mucosa. This fact was confirmed in animal experiments, and the effect of the mucin used in the present invention on elimination of Hp from the stomach was observed. Therefore, the mucin can be used as an inhibitor of Hp colonization in the stomach and is useful for preventing or treating diseases caused by or associated with *Helicobacter pylori* such as peptic ulcers. The mucin used in the present invention is naturally-occurring occurring and is very safe.

Accordingly, mucin can be used as an inhibitor of Hp colonization to be formulated into a medication or food. Especially, mucin from milk or albumen of chicken eggs has been eaten in the past, so it can be formulated into foods such as an anti Hp functional food, a health food, and a food for medical use having anti Hp activity.

The inhibitor of Hp colonization of the present invention may be formulated together with a pharmaceutically acceptable carrier or excipient to form a pharmaceutical composition. If necessary, other additives or agents may be added. For example, antacids (e.g., sodium hydrogencarbonate, magnesium carbonate, precipitated calcium carbonate, synthetic hyrotalsite), agents for protection of gastric mucosa (e.g., synthetic aluminum silicate, sucralfate, and sodium copper chlorophyllin) and digestive enzymes (e.g., biodiastase or lipase) may be added to the pharmaceutical composition. The preparation of a pharmaceutical composition may be carried out in conventional ways. The administration of the inhibitor of the present invention may be by an oral route. The dosage of the inhibitor of the present invention is selected according to the usage, purpose and conditions of symptoms. Usually, 0.6–2.6 g of the mucin (as a dry weight) may be administered per day for an adult, and preferably 1–2 g of the mucin may be administered per day for an adult.

Additionally, the inhibitor of Hp colonization comprising a mucin may be used along with an inhibitor of gastric acid secretion. The combination of a mucin and an inhibitor of gastric acid secretion is more effective in eliminating Hp from the stomach than a mucin alone. Examples of the inhibitor of gastric acid secretion used in the present invention include $H_2$ inhibitors such as famotidine, nizatidine, roxatidine, ranitidine or cimetidine and proton pump inhibitors such as omeprazol, lansoprazol or sodium rabeprazole. The dosage of the inhibitor of gastric acid secretion may be preferably 20–30 mg per day for an adult.

When the mucin is used as an additive to a physiologically functional food or a food for medical use, usually about 0.5–5.0 wt % of the mucin may be contained in the food and preferably about 1–3 wt % may be contained in the food. The kind of physiologically functional food is not limited, and foods which can be ingested continuously such as sweets, powdered soups, and beverages are preferred. As an example of foods for medical use, a liquid food is preferred. Such a food may be prepared by adding to a mucin excipients such as dextrin, adhesives such as sodium casein, and if desired, nutrients such as vitamins and minerals, emulsifiers, stabilizers, and spices. Also, the mucin may be added to a food such as a soup, beverage, or liquid food to prepare various forms of foods for medical use. When the mucin is utilized as a health food, the mucin may be contained as an active ingredient in an amount of about 30–60 wt % of the food. The mucin may be formulated together with excipients such as lactose, cornstarch, crystalline cellulose, and PVP, with binders, and, if desired, with nutrients such as vitamins and minerals into various forms such as fine particles, tablets, and granules.

The following examples are given to further illustrate the present invention. It should be understood that the present invention is not limited to the specific details set forth in the examples.

EXAMPLE 1

Preparation of Mucin From Milk

As the milk of a cow, about 1,000 ml of milk produced immediately after parturition (colostrum) and about 1000 ml of milk produced 10 days after parturition were prepared. Each was centrifuged at 10,000 r.p.m. at 4° C. for 30 minutes so as to remove milk fat, and the supernatant was recovered. Then, to the supernatant, 1M acetic acid was added dropwise until the pH was 4.5 so as to remove casein. After the milk was allowed to stand for 1 hour at room temperature, casein was removed by centrifugation to obtain whey. Then, in order to remove lipoprotein, the whey was adjusted to a pH of 7 with 1N NaOH, and to this 0.1 ml of 1M $CaCl_2$ and 0.02 ml of 10% dextran sulfate-500 were added per 1 ml of the whey. After the liquid was allowed to stand for 1 hour at room temperature, centrifugation was conducted at 10,000 r.p.m. at 4° C. for 30 minutes to obtain a supernatant. Each supernatant was concentrated to about one-twentieth volume and dialyzed against 100 fold amount of purified water and stored below −30° C. until use.

In order to purify mucin (glycoprotein) from the above whey, each sample was applied to a Sepharose C1-2B gel column equilibrated with 50 mM Tri-HCl buffer (pH 8.0) containing 0.15M NaCl+2 mM EDTA+0.02% $NaN_3$ and fractionated to take 10 ml fractions in fraction collectors. The fractions were divided into four fractions, F1, F2, F3 and F4 according to the elution pattern of protein. Each fraction was analyzed by SDS-PAGE, and as a result, the fraction F1 was confirmed to be a giant molecule containing glycoprotein in a high concentration. There was no particular difference between molecules derived from colostrum and molecules derived from milk following colostrum with respect to the content of the glycoprotein in the giant molecule. Accordingly, milk following colostrum was used for purification of mucin in large amounts because of its availability, and about 100 mg (dry weight) of mucin was obtained from 1,000 ml of milk.

EXAMPLE 2

Preparation of Mucin Derived From Albumen of Chicken Eggs (Ovomucin)

From 50 unfertilized eggs of White Leghorn hens within a week after being laid, only albumen was collected and was sieved to separate concentrated albumen. A gelatinous portion obtained by ultracentrifugation (100,000 g×60 minutes) was washed repeatedly with 2% KCl to prepare insoluble ovomucin. After being washed with purified water, ovomucin was suspended in Mensel buffer (pH 9.5, ionic strength= 0.01) and solubilized by ultrasonic wave treatment in 100 W, 9 $KH_2$ (2° C.) for 10 minutes. This solubilized product was applied to a Sepharose CL-2B gel column to recover an F1 fraction as described in Example 1 (Preparation of mucin from milk). The F1 fraction was analyzed by SDS-PAGE and was shown to contain glycoprotein at a high concentration like milk-derived mucin. The molecular weight thereof was about $5.5–8.3×10^6$. About 2,000 mg (dry weight) of mucin derived from the albumen of chicken eggs was recovered to be used in the following experiment.
Experiment 1 In vitro Experiment Inhibitory effects on colonization of urease produced by Hp to gastric mucosa were examined in an in vitro experiment system when using milk-derived mucin prepared in Example 1 and albumen-derived mucin prepared in Example 2.

For comparison, fucoidan (Sigma), a kind of polysaccharide derived from Nemacystus, which is described in Japanese Patent Application Kokai No. 7-138166 as an inhibitor of Hp colonization, was used. The in vitro experiment system described in that publication is constructed on the assumption that an adhesin of Hp is fucose, and that publication does not show that fucoidan has an inhibitory effect on Hp colonization when administered to mice infected with Hp.
(Materials and Methods)

The present inventors had already found that an adhesin of Hp is urease produced by Hp. Since this urease binds well to mucin of gastric mucosa, porcine gastric mucin to be used for urease adhesion test was prepared as follows.
Preparation of Porcine Gastric Mucin Healthy pigs about two months old were slaughtered, and their stomachs were recovered and washed on the insides thereof with PBS (pH 7.4) containing 0.1M phosphate+ 0.15M NaCl+5 mM N-ethyl maleimide (NEM)+1 mM phenylmethylsulfonyl fluoride (PMSF)+1 mM EDTA. The stomachs were incised, and gastric mucosa was scraped and suspended in the above-mentioned buffer. This suspension of mucosa was homogenized by a Polytron homogenizer while being iced and was centrifuged at 15,000×g to recover supernatant. The supernatant was centrifuged again at 25,000×g to recover supernatant, which was dialyzed against distilled water and lyophilized to obtain crude gastric mucin. Then, this lyophilized crude gastric mucin was dissolved in PBS (pH 6.8) containing 6M guanidine hydrochloride and protease inhibitor (5 mM NEM, 1 mM PMSF, 1 mM EDTA), and overlaid on a cesium chloride density gradient (1.5 g/ml) and centrifuged at 34,000×g for 48 hours.

A cyanuric acid-containing fraction was detected by nitrocellulose membrane blotting and drying with periodic acid Schiff's reagent. Dyed fractions were pooled and overlaid on a cesium chloride density gradient and centrifuged. Dying-positive fractions were pooled and lyophilized. Then, the lyophilized product was subjected to gel filtration through Sepharose CL-4B column equilibrated with 0.1M phosphate buffer (0.1M NaCl, pH 6.8) to carry out fractionation. Fractions which were PAS dying-positive and had proteins at a high concentration were pooled and dialyzed against PBS (pH 6.8) to obtain purified porcine gastric mucin, which was stored at –80° C. until use. The obtained gastric mucin was confirmed to be glycoprotein of 66 kD by SDS-PAGE.
Urease Adhesion Test to Porcine Gastric Mucin A microplate for a urease adhesion test was prepared as follows.

To each well of a 96 well microplate, a 100 μl portion of 1.25% glutaraldehyde solution was added, and sensitization was conducted for 5 minutes. After washing each well three times with distilled water, a 50 μl portion of purified porcine gastric mucin (1.27 mg/ml) was added to each well and was subjected to immobilization by standing overnight at 4° C.

When the microplate is used, blocking was conducted by adding 3% BSA to each well to react at 37° C. for 60 minutes, and then the plate was washed three times with PBS supplemented with 0.05% Tween 20.

A urease adhesion test was carried out using the microplate prepared above as follows, in order to observe adhesion of urease to porcine gastric mucin immobilized on the microplate.

Purified biotinylated urease was diluted so as to give a final concentration of 7.0 μg/ml with adhesion media having different pH ranges (20 mM phosphate buffer containing 0.01% Tween 20 and 0.15M NaCl, pH adjusted to be 2.0, 3.0, 4.0, 4.5, 5.0, 5.5, 6.0 or 6.5). Each urease sample thus prepared was added to 2 wells of mucin-immobilized microplate mentioned above to conduct sensitization at 37° C. for 60 minutes. Then, immediately after each well was washed three times with the adhesion medium, 10% neutral formalin (pH 7.4) was added to each well, and the plate was allowed to stand at 37° C. for 30 minutes to perform fixation. In order to determine the amount of urease adhered to the well, streptoavidin HRP was added to each well to react at 37° C. for 60 minutes. Then, ortho-phenylenediamine 2HCl as a substrate and $H_2O_2$ were added to react. 3N $H_2SO_4$ was used for termination of the reaction. Known amounts of urease diluted serially 2-fold were placed In running plate and a calibration curve thereof was used to determine the amount of urease in a sample.
Inhibition Test of Urease Adhesion Inhibition tests of urease adhesion were conducted using mucins of the present invention (mucins from milk and albumen of chicken eggs) and fucoidan (comparative example). First, samples having various concentrations were each mixed with biotinylated urease, and each mixture was shaken at 37° C. for 60 minutes to carry out sensitization. Then, this mixture was transferred to each well of a 96 well-microplate immobilized with porcine gastric mucin, and the plate was shaken at 37° C. for 60 minutes to carry out sensitization. Then, each well in the microplate was washed three times with adhesion medium (pH 3.0) and was fixed by heating at 65° C. for 10 minutes. The fixed wells were washed three times with PBS-Tween 20 (0.5%) (pH 6.8), and strepto-avidin HRP was added to each well, and biotinylated urease adhered to porcine gastric mucin was detected by ELISA described above.

Results
Urease Adhesion Pattern to Purified Gastric Mucin

As shown in FIG. 1, urease adheres specifically to porcine gastric mucin, and this adhesion pattern depends on pH. Since urease adhesion reaction at about pH 3.0 is considered to reflect the colonization character of Hp in gastric mucosa, a substance which is able to inhibit the adhesion of urease in this pH range may inhibit the colonization of Hp in the stomach.

Inhibition of Urease Adhesion With Mucin

Figure 2:
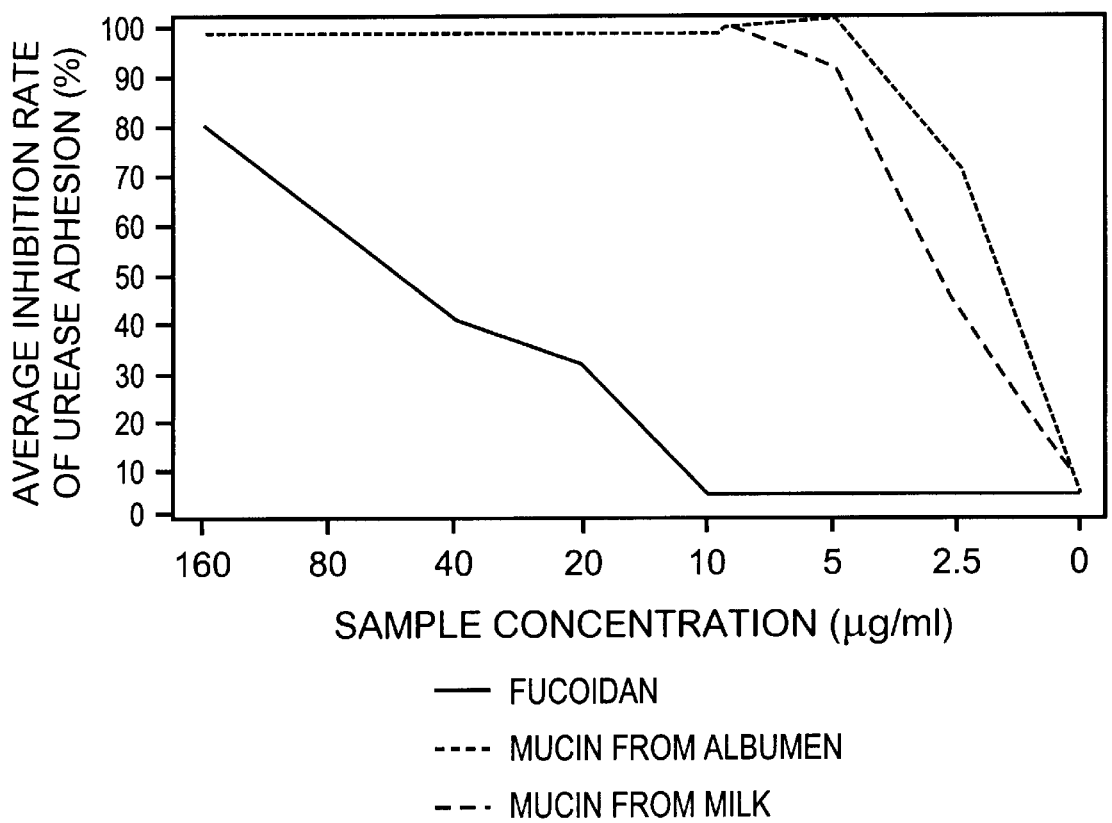
FIG. 2 is a graph showing the inhibition rate of urease adhesion.

As shown in FIG. 2, urease adhesion to porcine gastric mucin was inhibited dose-dependently with mucin derived from milk and mucin derived from albumen of chicken eggs, while fucoidan exhibited a low capacity for inhibition of urease adhesion. Urease is localized on the surface of Hp cells, and therefore the mucins of the present invention can inhibit infection with Hp, that is to say, eliminate Hp from the stomach by binding to urease of the cells and masking urease, an adhesin, in the stomach.

Experiment 2 In vivo Experiment

This experiment was performed to further confirm the result of Experiment 1.

(Method)

The experimental animal was a hairless mouse (NS:Hr/ICR, Research Institute for Human and Animal Propagation, Accession No. IRA-NHI-9701) (ATCC #72024) (Clin. Diagn. Lab. Immunol. 5: 578–582, 1998) having a high sensitivity to Hp infection. Each of a plurality of hairless mice was challenged with $1 \times 10^9$ CFU of NSP 335 by oral administration. After breeding for a week, the mice were administered samples dissolved in drink at various concentrations for 4 weeks. A control group was administered a drink containing no sample. The number of mice in each group was 10, and the amount of the drink was 4–8 ml per day and per mouse. After the completion of administration of the samples, the mice in each group were slaughtered. The stomachs of the mice were recovered, and after removal of the contents, the stomachs were washed eight times with PBS (pH 7.2) by a vortex mixer and homogenized by a homogenizer to form an emulsion, which was used for detection Hp. The detection of Hp was carried out by placing the emulsion on a medium for detecting Hp (Poremedia Hp isolation medium, Eiken Kagaku), incubating at 37° C. for 5 days by the gas pack method, and counting colonies.

(Results)
Effects of Milk-Derived Mucin and Albumen-Derived Mucin on Elimination of Hp in Hp-Colonized Mice As shown in FIG. 3, milk-derived mucin and albumen-derived mucin could eliminate Hp from the stomach in a concentration-dependent manner. On the other hand, fucoidan did not exhibit remarkable effects on inhibition of Hp colonization, unlike the mucins of the present invention. 100% of mice (10/10) in the control group were infected with Hp. From these results it is supposed that milk-derived mucin and albumen-derived mucin can inhibit infection with Hp by binding predominantly to urease produced by Hp and masking urease, an adhesin.

Experiment 3 In vivo Experiment

This experiment was conducted in animals to demonstrate synergistic effects obtained by combination of a mucin and an inhibitor of gastric acid secretion ($H_2$ inhibitor or proton pump inhibitor). In this experiment, mucin from milk which exhibited a high rate of elimination in Experiment 2 was used as a mucin. The same procedure as in Experiment 2 was used except that an $H_2$ inhibitor (famotidine) or a proton pump inhibitor (omeprazol) was orally administered by force for one week from one week after the challenge, and the mucin from milk was orally administered in a drink for two weeks from one week after the challenge. Table 1 shows the effects of eliminating Hp from the stomach.

TABLE 1

| Administered Group | uninfected mice | % rate of elimination |
|---|---|---|
| mucin from milk (2.0 μg/ml) + famotidine (200 μg/ml) | 6/6 | 100 |
| mucin from milk (2.0 μg/ml) + omeprazol (15 μg/ml) | 5/6 | 83.3 |
| Control Group | 0/0 | 0 |

As shown in Table 1, the combination of a mucin and an inhibitor of gastric acid secretion exhibits a high rate of elimination even though the period of administration was short and the amount of the mucin was less than in Experiment 2, which means that the combination is more effective than mucin alone.

The milk-derived mucin prepared in Example 1 was used as a mucin in the following preparation examples.

Preparation 1 (Food)

(Chewing gum)

| | |
|---|---|
| gum base | 25.0 |
| calcium carbonate | 2.0 |
| sorbitol | 54.0 |
| mannitol | 16.0 |
| flavor | 1.0 |
| mucin | 1.0 |
| water | q.s. to 100.0 (% by weight) |

(ice cream)

| | |
|---|---|
| cream (40% fat content) | 32.54 |
| milk (3.7% fat content) | 33.16 |
| defatted evaporated milk | 16.08 |
| sugar | 11.75 |
| corn syrup | 4.67 |
| stabilizer | 0.3 |
| mucin | 1.5 |
| total | 100.0 (% by weight) |

(powdered soup)

| | |
|---|---|
| powdered bean for cooking | 66.5 |
| wheat flour | 3.5 |
| wheat embryo | 2.5 |
| dry yeast powder | 2.5 |
| onion powder | 4.8 |
| meat extract powder | 15.5 |
| salt | 0.2 |
| spices (white pepper, etc.) | 1.8 |
| seasonings (amino acid, etc.) | 0.2 |
| mucin | 2.5 |
| total | 100.0 (% by weight) |

(dried soup) 10.0 g/200 ml

| | |
|---|---|
| chicken egg | 3.6 |
| meat extract | 1.0 |
| onion extract | 1.7 |
| carrot paste | 2.1 |
| kombu extract | 0.1 |
| emulsifier | 0.1 |
| salt | 0.2 |
| spice (red pepper) | 0.2 |
| seasonings (amino acid, etc.) | 0.2 |
| mucin | 0.8 |
| total | 10.0 g |

Preparation 2 (Health Food)

Formula 1: in 100 g of fine particles

| | |
|---|---|
| mucin | 45 g |
| lactose (200M) | 35 g |

-continued

| | |
|---|---|
| corn starch | 15 g |
| PVP (K-30) | 5 g |

These components were formulated into fine particles by a conventional wet granulation method.

| Formula 2: in 100 g of granules | |
|---|---|
| mucin | 33 g |
| lactose (200M) | 44 g |
| cornstarch | 18 g |
| PVP (K-300) | 5 g |

These components were formulated into granules by a conventional extrusion granulation method.

| Preparation 3 (Food from Medical Use) | |
|---|---|
| liquid food (200 ml/pack) | |
| mucin | 2.6 |
| maltodextrin | 39.0 |
| casein Na | 13.0 |
| vegetable oil | 12.0 |
| vitamins | 1.0 |
| minerals | 1.5 |
| emulsifier | 0.2 |
| milk protein | 10.3 |
| sodium phosphate | 1.8 |
| potassium phosphate | 1.2 |
| flavor | 0.5 |
| stabilizer (carrageenan) | 1.5 |
| water | q.s. to 100.0 (% by weight) |
| Tonic (soup type) | |
| mucin | 2.5 |
| carrot (carrot paste) | 10.0 |
| heavy cream | 12.0 |
| lactose | 1.8 |
| onion (onion extract) | 1.5 |
| milk protein powder | 0.5 |
| milk oligosaccharide | 1.5 |
| consomme powder | 0.5 |
| wheat embryo | 0.5 |
| eggshell calcium | 0.2 |
| whey calcium | 0.1 |
| salt | 0.2 |
| emulsifier | 0.2 |
| water | q.s. to 100.0 (% by weight) |

As is apparent from the above, in accordance with the present invention, a safe and effective inhibitor of Hp colonization and food containing the inhibitor are provided. Therefore, diseases such as peptic ulcers caused by Hp can be suppressed effectively without the occurrence of side effects. As a starting material of mucin used in the present invention, milk or chicken eggs which can be obtained inexpensively and in large amounts may be used to prepare in a simple way mucin which exhibits superior effects. Also, unlike antibiotics which have been used for treatment of peptic ulcers, mucin can eliminate Hp specifically from the stomach without the problem of producing drug-resistant bacteria.

What is claimed is:

1. An inhibitor of *Helicobacter pylori* colonization, comprising as an active ingredient a mucin derived from whey of bovine milk.

2. An inhibitor of *Helicobacter pylori* colonization, comprising as an active ingredient a mucin which is prepared by removing milk fat and casein from bovine milk to obtain whey, which is subsequently subject to removal of lipoproteins, concentration, and treatment for purification of mucin.

3. An inhibitor according to claim 2, wherein the treatment for purification of mucin is treatment with membrane.

4. An inhibitor of *Helicobacter pylori* urease, comprising as an active ingredient a mucin derived from whey of bovine milk, wherein said mucin is capable of binding the urease specifically.

5. An inhibitor composition of *Helicobacter pylori* colonization, comprising a mucin derived from whey of bovine milk and an inhibitor of gastric acid secretion.

6. An inhibitor composition of *Helicobacter pylori* urease, comprising a mucin derived from whey of bovine milk and an inhibitor of gastric acid secretion, wherein said mucin is capable of binding the urease specifically.

7. A food comprising the inhibitor of *Helicobacter pylori* colonization according to claim 2.

8. A food according to claim 7, wherein the mucin is present in an amount of 0.5–60% by weight of the food.

9. A method for inhibiting *Helicobacter pylori* colonization in mammals including humans, comprising orally administering to a mammal a mucin derived from whey of bovine milk in an effective amount for inhibiting *Helicobacter pylori* colonization.

10. A method for inhibiting *Helicobacter pylori* urease in mammals including humans, comprising orally administering to a mammal a mucin derived from whey of bovine milk in an effective amount for inhibiting *Helicobacter pylori* urease, wherein said mucin is capable of binding the urease specifically.

11. A method for inhibiting *Helicobacter pylori* colonization in mammals including humans, comprising orally administering to a mammal a mucin derived from whey of bovine milk and an inhibitor of gastric secretion in an effective amount for inhibiting *Helicobacter pylori* colonization.

12. A method for inhibiting *Helicobacter pylori* urease in mammals including humans, comprising orally administering to a mammal a mucin derived from whey of bovine milk and an inhibitor of gastric acid secretion in an effective amount for inhibiting *Helicobacter pylori* urease, wherein said mucin is capable of binding the urease specifically.

13. A method for preventing or treating a disease caused by or associated with *Helicobacter pylori* in mammals including humans, comprising orally administering the inhibitor according to claim 1 to a mammals in an effective amount for preventing or treating the disease.

14. A method for preventing or treating a disease caused by or associated with *Helicobacter pylori* in mammals including humans, comprising orally administering the inhibitor according to claim 2 to a mammal in an effective amount for preventing or treating the disease.

15. A method for preventing or treating a disease caused by or associated with *Helicobacter pylori* in mammals including humans, comprising orally administering the inhibitor according to claim 3 to a mammal in an effective amount for preventing or treating the disease.

16. A method for preventing or treating a disease caused by or associated with *Helicobacter pylori* in mammals including humans, comprising orally administering the inhibitor composition according to claim 5 to a mammal in an effective amount for preventing or treating the disease.

* * * * *

UNITED STATES PATENT AND TRADEMARK OFFICE
CERTIFICATE OF CORRECTION

PATENT NO. : 6,235,709 B1
DATED : May 22, 2001
INVENTOR(S) : Y. Kodama et al.

It is certified that error appears in the above-identified patent and that said Letters Patent is hereby corrected as shown below:

<u>Title page,</u>
The following correction is made:
-- [73] Assignee: Ghen Corporation, Gifu (JP)
                      Nisshin Flour Milling Co., Ltd., Tokyo (JP) --

Signed and Sealed this

Twenty-eighth Day of May, 2002

*Attest:*

*Attesting Officer*

JAMES E. ROGAN
*Director of the United States Patent and Trademark Office*